United States Patent [19]

Spielvogel et al.

[11]  4,312,989

[45]  Jan. 26, 1982

[54] PHARMACOLOGICALLY ACTIVE AMINE BORANES

[75] Inventors: Bernard F. Spielvogel; Andrew T. McPhail, both of Durham; Iris H. Hall, Chapel Hill, all of N.C.

[73] Assignee: The United States of America as represented by the Secretary of the Army, Washington, D.C.

[21] Appl. No.: 68,356

[22] Filed: Aug. 21, 1979

[51] Int. Cl.$^3$ .......................... A61K 31/69; C07F 5/02
[52] U.S. Cl. ............................... 546/13; 260/465.5 R; 560/155; 562/565; 564/8; 424/248.4; 424/248.53; 424/248.54; 424/263; 424/304; 424/311; 424/319; 424/320; 424/325
[58] Field of Search ................ 560/169, 155; 562/565; 260/583 A, 465.5 R, 561 A; 546/13; 564/8

[56] References Cited

PUBLICATIONS

Spielvogel, J. Am. Chem. Soc., 98, pp. 5702-5703, (1976).
Surjit, J. Chem. Soc., D., p. 1619, (1970).
Wisian-Neilson, Inorg. Chem., 17, pp. 2327-2329, 1978).
Weidig, Inorg. Chem., 13, pp. 1763-1768, (1974).
Wilson, "Textbook of Organic Medical and Pharmaceutical Chemistry", pp. 39-40, (1954).

Primary Examiner—Natalie Trousof
Assistant Examiner—Michael Shippen
Attorney, Agent, or Firm—William G. Gapcynski; Werten F. W. Bellamy; John M. Petruncio

[57] ABSTRACT

The use of amine boranes to inhibit the inflammation process is disclosed. These boranes, which are boron analogs of α-amino acids, effectively block the following: general inflammation, induced arthritis, and the writhing reflex associated with inflammation pain. The inflammation associated with pleurisy is also inhibited. The boron analogs are shown in vitro to inhibit the release of lysosomal enzymes from liver and polymorphonuclear neutrophils (PMNs). Further, prostaglandin synthesis is blocked by these compounds at a low concentration, viz, $10^{-6}$M.

Liver oxidative phosphorylation processes are also uncoupled by these compounds, but PMN migration is unaltered at $10^{-4}$M. The elevation of cyclic adenosine monophosphate in PMNs correlates positively with in vivo antiarthritic activity. Studies in rodents demonstrate that these boron analogs may be used at safe therapeutic doses. Several compounds per se are included within the scope of the invention.

7 Claims, No Drawings

PHARMACOLOGICALLY ACTIVE AMINE BORANES

BACKGROUND OF THE INVENTION

While studying the metabolic effects of amine boranes on tumor cell metabolism, it was seen that these compounds interfered with oxidative phosphorylation processes of mitochondria, inhibited lysosomal enzymatic hydrolytic activities, and elevated cyclic adenosine monophosphate levels (cAMP). Since commercially available anti-inflammatory agents (e.g., phenylbutazone, salicylates, and indomethacin) have similar effects on cellular metabolism, it was decided to test the amine boranes for anti-inflammatory activity in rodents.

DETAILED DESCRIPTION OF THE INVENTION

The amine boranes of this invention which are useful for inhibiting the inflammation process may be represented by the following formulas:

$$R_3N.BH_2X \quad (I)$$

where

X is selected from the group consisting of H, CN, $CONR^1R^2$, COOH, halogen (preferably I), and $COOR^3$;

R is alkyl having 1 to 4 carbon atoms, preferably methyl;

$R^1$ and $R^2$ can be the same or different and are H or alkyl (preferably alkyl having 1 to 10 carbon atoms and, more preferably, having 1 to 4 carbon atoms); and $R^3$ is alkyl, preferably having 1 to 10 carbon atoms and, more preferably, having 1 to 4 carbon atoms;

$$H_3N.BH_2X \quad (II)$$

or $RNH_2.BH_2X$ or $R_2NH.BH_2X$ where

X is selected from the group consisting of H, CN, and halogen (preferably I); and R is alkyl having 1 to 4 carbon atoms, preferably methyl;

$$amine.BH_2X \quad (III)$$

where

X is selected from the group consisting of H, CN, and COOH; and amine is selected from the group consisting of morpholine, N-methyl morpholine, pyridine, and cyanoethyldimethylamine; and $$(CH_2NY_2.BH_2X)_2 \quad (IV)$$

where

X is selected from the group consisting of CN, $CONR^1R^2$, and COOH, $R^1$ and $R^2$ can be the same or different and are H or alkyl (preferably alkyl having 1 to 10 carbon atoms and, more preferably, having 1 to 4 carbon atoms); and Y is hydrogen or alkyl having 1 to 4 carbon atoms (preferably methyl).

While many of the amine boranes per se are known in the art, nevertheless, several specific compounds are new and unobvious and are included within the scope of this invention. Specifically, the following compounds are included in this invention:
$[CH_2N(CH_3)_2.BH_2COOH]_2$,
$[CH_2N(CH_3)_2.BH_2CON(H)CH_2CH_3]_2$,
$C_5H_5N.BH_2COOH$,
$(CH_3)_3N.BH_2COOCH_2CH_3$,
$NCCH_2CH_2N(CH_3)_2.BH_2CN$, and
$(CH_2NH_2.BH_2CN)_2$.

EXPERIMENTAL CHEMISTRY

Consideration of the isoelectronic formalism between carbon and boron results in the prediction of boron analogs of dipolar α-amino acids, e.g., the boron analog of betaine—$(CH_3)_3NBH_2COOH$. Interest in these boron analogs lies mainly in their potential biological activity when compared with the enormous biological activity of the α-amino acids. A highly significant step toward demonstrating the existence of this class of compounds was the discovery of the synthesis of trimethylaminecarboxyborane, the protonated boron analog of betaine. The synthetic route to this compound is shown in equation-1.

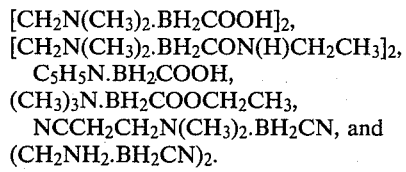
(1)

The acid $(CH_3)_3NBH_2COOH$, a white crystalline solid whose X-ray crystal structure was determined, is stable in air and $H_2O$.

AMINE-CYANOBORANES

One approach to the synthesis of boron analogs of the α-amino acids involves the conversion of the amine-cyanoborane to a boro-amino acid according to the procedure outlined in equation-1 above. To provide adequate quantities of the precursor amine-cyanoboranes, a general, high-yield synthesis of this class of compounds was developed as outlined in equation-2.

$$\text{Amine-HCl} + NaBH_3CN \rightarrow \text{amine}.BH_2CN + NaCl \quad (2)$$

Using this amine hydrochloride procedure, yields up to 90% have been obtained.

Following equation-2, amine-cyanoboranes have been prepared where the amine is $(CH_3)_3N$, $(CH_3)_2NH$, $CH_3NH_2$, $C_5H_5N$, $C_6H_5NH_2$, $pCH_3C_6H_4NH_2$, $NCCH_2CH_2N(CH_3)_2$, and $O(CH_2CH_2)_2NCH_3$. Bis(cyanoboranes) have been prepared from ethylenediamine (en) and tetramethylethylenediamine (TMED). While attempts to prepare the parent ammonia-cyanoborane by the above procedure were not successful, the parent compound was prepared by the base displacement reaction shown in equation-3.

(3)

$H_3NBH_2CN$ possesses considerable hydrolytic stability suffering only 8% loss of hydrogen in concentrated HCl after 70 hr at room temperature. In general, the amine-cyanoboranes are quite stable to air and moisture.

AMINE-CARBOXYBORANES

Using the general synthetic route illustrated by equation-1, amine.$BH_2COOH$ compounds where amine is pyridine and N-methyl morpholine have been prepared from the corresponding amine-cyanoborane. Likewise, TMED.$2BH_2COOH$ has been successfully synthesized. Furthermore, one can readily prepare derivatives of $(CH_3)_3NBH_2COOH$, as demonstrated by the preparation of the ethyl ester. The ethyl ester, a white solid, m.p. 45°–47° C., is prepared in 34% yield according to equation-4.

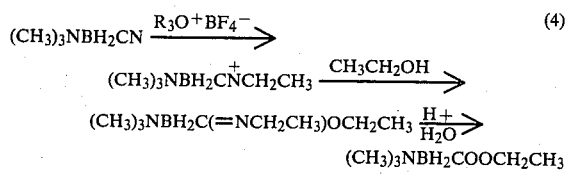

PHARMACOLOGICAL SCREENS

Toxicity studies

Acute $LD_{50}$ toxicity studies were carried out in $CF_1$ male mice (about 30 g) using the method of Litchfield et al., *J. Pharmacol. Exp. Ther.*, 96, 99 (1949).

Anti-inflammatory Screen $CF_1$ male mice (about 30 g) were administered test drugs at 10 mg/kg in 0.05% polysorbate 0.80-water intraperitoneally 3 hr and 30 min prior to 0.05 ml of 2% carrageenan in 0.9% saline injected into the plantar surface of the right hind foot. Saline injected into the left hind foot served as a base line. After 3 hr, both feet were excised at the tibiotarsal (ankle) joint according to the modified (Roszkowski et al., *J. Pharm. Exp. Ther.*, 179, 114 1971) method of Winter, resulting in an 87 mg net increase in the weight of the control animal's feet.

Anti-pyretic screen

Sprague Dawley rats (about 200 g) were administered 2 ml of a 44% solution of Baker's yeast subcutaneously (see Roszkowski et al., supra) 18 hr prior to the injection of drugs at 2.5 or 5 mg/kg intraperitoneally resulting in an elevation of 3.46° F. Alternatively, rats were administered 0.25 mg killed and dried *Mycobacterium butyricum* (Difco) (see Randall et al., *Arch int Pharmacodyn et De Ther*, 220, 94 1976) subcutaneously prior to the administration of drugs. Rectal temperatures were taken immediately prior to and 2, 4, and 6 hr after drug administration.

Writhing Reflex $CF_1$ male mice were administered test drugs at 20 mg/kg intraperitoneally 20 min (see Hendershat et al., *J. Pharmacol Exp. Ther.* 125, 237 1959) prior to the administration of 0.5 ml of 0.6% acetic acid (Vingar et al., *European J. Pharmacol*, 37, 23 1976). After 5 min the number of stretches, characterized by repeated contractures of the abdominal musculature accompanied by extension of the hind limbs, was counted for the next 10 min. The control mice had 78 stretch reflexes per 10 min.

Chronic Adjuvant Arthritic Screen

Male Sprague Dawley rats (about 160 g) were injected at the base of the tail with 0.2 ml of solution of killed and dried *Mycobacterium butyricum* and digitonin in mineral oil (see Waksman et al., *J. Immunol.*, 85, 403 1960). Test drugs were administered intraperitoneally commencing on day 3 through day 20 at 2.5 mg/kg/day. Animals were sacrificed on day 21, and the feet were excised and weighed. Control animals resulted in a net weight gain of 0.830 g.

Anti-Pleurisy Screen

Sprague Dawley rats were administered test drugs at 2.5 mg/kg intraperitoneally 1 hr before and 3 hr post injection of 0.05 ml of a solution of 0.316% Evan's blue and carrageenan into the pleural cavity (see Sancilio, *Prac. Soc. Exp. Biol.* and *Med.*, 127, 597 1968). Six hrs later, the rats were sacrificed and the fluid collected from the pleural cavity. Control rats produced 2.5 ml of fluids. Polymorphonuclear neutrophil (PMN) migration studies were carried out by the method of Nelson et al., *J. Immunol.*, 115, 1650 (1975). Analogs were tested in vitro at $10^{-4}$ M concentration.

*Ulcerogenic tests* were carried out in Sprague Dawley rats (about 160 g) which were administered test drugs intraperitoneally at 2.5 mg/kg for 3 weeks. After the food had been removed 18 hr, the last dose on day 21 was administered. Four hr later, the rats were sacrificed and the gastric and duodenum mucosa were examined for bleeding and/or ulcers (Brodie et al., *J. Gastrointernal*, 53, 604, 1967). In an analogous experiment, animals were bled on day 21 by tail vein and the red blood cells and white blood cells counted in a hemocytometer and expressed as number of cells $\times 10^6/cm^3$. Hematocrits were also obtained. See Lang et al., *J. Med. Chem.*, 19, 1404 (1976).

BIOCHEMICAL ASSAYS

Lysosomal enzymatic assays

Sprague Dawley rats (about 160 g) were sacrificed, the liver excised, and a 10% homogenate (4x) in 0.25 M sucrose and 0.001 M (ethylenedinitrilo) tetra acetic acid, ph 7.2 was prepared.

Polymorphonuclear neutrophils (PMNs) were collected from the peritoneal cavity four hr after the injection of 35 ml of 0.5% oyster glycogen in isotonic saline (Orange et al., *J. Exp. Med.*, 127, 767 1968). The PMNs were centrifuged down at 800 g for 20 min, washed, and resuspended in minimum essential medium (MEM) with 10% fetal calf serum pH 7.4.

Acid phosphatase activity (Gianetto et al., *Biochem J.*, 59, 433 1955) was carried out by incubating with 0.1 M $\beta$-glycerol phosphate in 0.1 M acetate, pH 5.0 with 5 $\mu$moles of test drugs in 1% carboxymethylcellulose (CMC) for 20 min with liver homogenate and 60 min with resuspended PMNs. Lysosome enzymes were released by 0.02% alkyl phenoxy polyethoxy ethanol-100 to obtain the total enzymatic activity. The reaction was stopped with 10% trichloroacetic acid and the solution centrifuged. Aliquots of the supernatant were assayed for inorganic phosphate content by the method of Chen et al., *Anal. Chem.*, 28, 1756 (1956). Percent free acid phosphatase was calculated. Cathepsin activity was determined in an analogous manner except the substrate used was 2% azocasein (Schleuning et al., *Methods in Enzymology*, XLV, 330 1976) in 0.1 M acetate buffer pH 5.0. The supernatant was assayed for acid soluble peptide fragments at 366 nm. Percent free cathepsin activity was calculated.

Cyclic-3', 5'-Adenosine Monophosphate Levels (cAMP)

Isolated PMNs were incubated with test drugs at 5 μmoles for 1 hr at 37° C. in MEM at pH 7.4. The reaction was stopped with 6% trichloroacetic acid. The cyclic-3',5'-adenosine monophosphate levels were determined by the radioimmunoassay of Gilman, *Proc. Natl. Acad. Sci.* (USA), 67, 305 (1970), using 3 H(G)-cyclic-3',5'-adenosine monophosphate (39.8 Cu/m mol). Results were calculated in p mole/$10^7$ PMNs cells.

Prostaglandin Synthetase Activity

The incubation medium of Tomlinson et al., *Biochem. Biophy Res. Commun.*, 46, 552 (1972), was used to determine $^3$H prostaglandin formation (PGE, PGFa, PGD) using $^3$H(N-) arachidonic acid (86.5 Ci/m mol) and 10 mg purified commercial prostaglandin synthetase from beef seminal vesicle. After 1 hr at 37° C. the reaction was stopped with 1 N HCl and extracted with ethyl ether and evaporated. The residue was taken up in ethyl acetate and spotted on silica gel TLC plates which were eluted with chloroform:methanol:water:acetic acid (90.8:1:0.8). See Glatt, et al., *Agents Action*, 7, 321 (1977). The plates were dried and developed in iodine vapor and with the use of prostaglandin standards the appropriate areas were scraped and counted for $^3$H content. Indometacin was used as a standard at $10^{-4}$M concentration. Test drugs were used at $10^{-6}$M.

Oxidative Phosphorylation Studies

Basal and adenosine diphosphate stimulated respiration on 10% liver homogenates as measured using succinate or αketoglutarate as substrate. See Glatt, et al., supra. The reaction vessel contained sucrose 55 μmoles, KCl 22 μmoles, $K_2HPO_4$ 22 μmoles, test compounds at 5 μmoles in 1% CMC and sodium succinate 90 μmoles or αketoglutarate 60 μmoles in a total volume of 1.8 ml. After the basal metabolic (state 4) level was obtained, 0.257 μmoles of adenosine diphosphate was added to obtain the adenosine diphosphate stimulated rate (state 3). The rate of respiration was calculated at μl of $O_2$ consumed/hr/mg wet weight of liver.

RESULTS

The boron analogs afforded significant anti-inflammatory activity in rodents. Administration of compounds I, V and VI (see Table I) resulted in at least 50% inhibition of the carrageenan induced edema in mouse foot pads (Table II), while compounds II, X, XII and XVII resulted in at least 40% inhibition. The administration of compounds II, V and X caused 80% inhibition of the writhing reflex which is similar to inflammation pain. Compounds VI, VII and VIII caused 70% inhibition of the reflex. In the rat induced arthritic screen after 3 weeks of dosing, compounds III, V, X, XIV, and XIX caused better than 80% inhibition, X caused 100% inhibition, and V caused 96% inhibition. Compound V was administered intraperitoneally from 1.25 to 10 mg/kg/day. Doses at 1.25 mg/kg/day caused 75% inhibition, 2.5 mg/kg/day, 96% inhibition, and 5 or 10 mg/kg/day, 100% inhibition. Compounds VI, IX, XIII, and XVIII afforded better than 70% inhibition of the induced arthritic state and compounds II and XVII caused 60% inhibition. In the antipyretic test compound V at 5 or 10 mg/kg resulted in no inhibition of elevated body temperature. In the anti-pleurisy screen, compound III demonstrated 33%, V 35%, X 49% and XIX 39% inhibition. Boron analogs had no effect on the chemotaxic migration of PMNs. Dosing for three weeks with II, V, X, XIV and XIX intraperitoneally resulted in no alteration of the red blood or white blood cell count/cu mm and no gastric or duodenum mucosa irritations or bleeding.

Percent free lysosomal enzymatic activities in liver and PMNs were inhibited by the presence of boron analogs (Table III). Free acid phosphatase activity in liver was inhibited between 28 and 34% by III, V, IX, X, XII, XIV and XIX while in PMNs compound III caused 43% inhibition, V 65%, VIII 50%, X 66%, and XIV 50% inhibition. Free proteolytic cathepsin activity of liver was inhibited at least 75% by III, IX, XII, XIV and XIX with 100% by V and 97% by X. PMN cathepsin activity was inhibited at least 82% by III, VIII, X, XI, XVIII, and XIX with 95% by V and 100% by X.

Cyclic adenosine monophosphate levels in PMNs were elevated after in vitro incubation with drugs (Table III). Compound III caused a 45%, V a 145%, IX a 33%, X a 261%, XII a 55%, XIV a 65% and XIX a 99% increase.

In vitro a $10^{-6}$ M concentrations, compounds III, V, VI, IX, X, XII, XIV, XV, XVII and XIX blocked prostaglandin synthesis greater than 30% (Table IV). Compound X resulted in 58% inhibition and XIV 62% inhibition. The presence of boron analogs at 5 μmoles caused uncoupling of oxidative phosphorylation processes of liver mitochondria. A few agents suppressed basal (state 4) as well as adenosine diphosphate stimulated respiration (state 3) with both substrates, e.g. XX. Uncoupling of the electronic transport chain is seen with succinate, a flavin adenine dinucleotide dehydrogenase, with compounds I–X, XII, and XV–XVIII. This can be observed as an increase in state 4 respiration and a decrease in state 3 respiration. With α-ketoglutarate a substrate, a nicotinamide diphosphate linked dehydrogenase, uncoupling can be seen with I, VI, VII, VIII, XII and XIII. Both states 3 and 4 respiration was inhibited with succinate in the presence of XII, XIV, XIX and XX and with α-ketoglutarate by III, IV, V and XX. Compounds which demonstrated potent antiarthritic activity also demonstrated potent inhibitory effects on state 3 respiration, e.g. III, V, X, XII, XIV and XIX using either succinate or α-ketoglutarate. The exception to this observation is XX.

DISCUSSION

Inflammation is a process which is associated with the release of chemical vasoamines, e.g., histamine, serotonin, slow reacting substance, and bradykinin, the release of lysosomal hydrolytic enzymes by leukocytes, the synthesis and release of prostaglandins, and the modulation of cyclic nucleotide levels of lymphocytes and leucocytes. These agents in turn cause increased vascular permeability, chemotaxis of PMNs and macrophages, erythema, dermatitis, hypersensitivity, complement fixation, allergy reactions, edema, and elicit pain along with increasing local and body temperature. The commercially available anti-inflammatory agents are known to interfere with some of the above processes, thus retarding the development of inflammation. For example, indomethacin decreases PMN motility, uncouples oxidative phosphorylation processes, inhibits prostaglandin synthetase and histidine decarboxylase activities, mucopolysacchric biosynthesis, platelet function, stabilizes lysosomal membranes and thus inhibits hydrolytic enzymatic acitivity. A number of agents are known to inhibit cyclic adenosine monophosphate phosphodieseterase activity and cause an increase in cyclic adenosine monophosphate, which supposedly stabilizes lysosomal membranes and blocks IgE dependent antigen induced vasoamine release and hypersensitivity. As can be seen from the current studies, those compounds which have potent anti-arthritic effects (e.g., compounds III, V, X, XII, XIV and XIX) also were significant inhibitors of lysosomal free hydrolytic activity, both from the liver and PMNs, indicating membrane stabilization. The inhibition of cathepsin activity was particularly high by the boron analogs. Increased levels of activity of this enzyme has been linked with a number of inflammation states. The boron analogs at the same construction as indomethacin were more effective in inhibiting PMN lysosomal rupture.

Prostaglandin synthetase activity was also suppressed by these same agents, III, V, X, XII, XIV and XX at $10^{-6}$ M. Indomethacin at $10^{-6}$ M concentration resulted in only 24% inhibition in this enzymatic system and at $10^{-4}$ M concentration, indomethacin caused 36% inhibition. The boron analogs V, X, XIV, XV, XVII and XIX were more potent than indomethacin in inhibiting prostaglandin synthesis by the isolated enzyme system. Oxidative phosphorylation processes were uncoupled at concentrations of 5 $\mu$moles for the boron compounds which demonstrated potent in vivo anti-arthritic activity in rats. The uncoupling and suppression of energy production needed for migration and phagocytosis of PMNs and macrophages was seen with all of the boron analogs; however, the PMN migration at $10^{-4}$ M demonstrated no inhibition by boron analogs. Thus it was more difficult to demonstrate positive correlation of uncoupling of respiration with in vivo anti-arthritic activity. Nevertheless, excluding compound XX, it can be seen that those compounds possessing potent anti-arthritic activity all suppressed adenosine diphosphate stimulated respiration (state 3) 40% or better. The effects of boron analogs on respiration may be secondary to other metabolic effects. A more positive correlation between in vivo anti-arthritic activity can be seen with the ability of the drug to elevate intracellular levels of cyclic adenosine monophosphate which could account for the ability of these agents to block lysosomal enzyme release and prostaglandin synthesis and release. Elevated levels of cyclic adenosine monophosphate have been correlated with the ability to block the release of lysosomal enzymes. Toxicity and side effects were not a problem with boron analogs at the required therapeutic doses.

While the use of amine boranes to inhibit the inflammation process has been demonstrated herein using mice and rats, it is believed that any animal which has inflammation can be treated successfully with our amine boranes. The appropriate therapeutically effective dose can be determined readily, and will usually be within about 0.01 mg/kg to about 200 mg/kg of animal body weight. Preferably, the dose will be within about 0.5 mg/kg to about 100 mg/kg of animal body weight, and more preferably within about 1.25 mg/kg to about 20 mg/kg of animal body weight. The mode of administration may be any suitable route, the intraperitoneal route being merely exemplary.

PREPARATIVE EXAMPLES

Working examples which show the preparation of compounds XI, XII, XIII, XVI, XVIII, XIX, and XX follow:

$N,N,N^1,N^1$-Tetramethylethylenediamine-bis(cyanoborane)

Sodium cyanotrihydroborate (9.6 g, 154 mmol) and TMED 0.2 HCl (14.6 g, 77 mmol) were allowed to react in refluxing THF for 100 hr until evolution of hydrogen was complete. The reaction mixture was filtered and the solids were stirred in $H_2O$ for 20 min to remove NaCl. The water insoluble white solid, which was collected by filtration, recrystallized from $CH_3CN$ and $H_2O$, and dried in vacuo (100° C., 48 h), was identified as XI by $^1H$ NMR, IR, and elemental analysis. Yield: 13.1 g, 88%.

$N,N,N^1,N^1$-Tetramethylethylenediamine-bis(carboxyborane)

A solution of XI (34.5 g, 178 mmol) and $Et_3OBF_4$ (550 ml, ca. 1.25 M in $CH_2Cl_2$) was allowed to reflux for 24 hr. After removal of $CH_2Cl_2$ in vacuo, the residual solid was stirred with $H_2O$(250 ml) for 72 hr. A white precipitate was collected by filtration but IR analysis indicated incomplete reaction due to the presence of small amounts of compound XIII. This solid was then stirred with 1 N HCl (100 ml) for 16 hr to yield a white solid which was dried in vacuo (100°, 48 hr) and was identified as XII. Yield: 24.7 g, 60%.

$N,N,N^1,N^1$-Tetramethylethylenediamine-bis(N-ethylamidoborane)

A solution of XI (17.2 g, 89 mmol) and $Et_3OBF_4$ (285 ml, ca 1.25 M in $CH_2Cl_2$) was allowed to reflux for 24 hr. The solution was cooled and 1 N NaOH was added slowly with vigorous stirring until pH=6.5. The organic layer was separated and the aqueous solution was extracted with $CH_2Cl_2$(3×100 ml). The combined organic extracts were dried over $MgSO_4$ and filtered. Removal of $CH_2Cl_2$ at reduced pressure resulted in a white solid which was identified as XIII. Yield: 11.3 g, 44%.

Pyridine-carboxyborane

A solution of pyridinecyanoborane (11.0 g, 93 mmol) and $Et_3OBF_4$ (175 ml, ca. 1 M in $CH_2Cl_2$) was allowed to reflux for 24 hr. The solution was cooled and $CH_2Cl_2$ was removed at reduced pressure leaving a viscous yellow colored oil. Water (50 ml) was added to the oil and the solution was allowed to stir at room temperature for 65 hr. A white solid was collected by filtration and the remaining aqueous solution was extracted with $CH_2Cl_2$ (3×75 ml). The combined extracts were dried over $MgSO_4$ and filtered. The solvent was removed in vacuo to give a yellow colored solid which was combined with white solid that had precipitated from the aqueous solution. Recrystallization from hot $H_2O$ gave white crystals of XVI. Yield: 3.95 g, 29%.

The ethyl ester (XVIII) was readily obtained by allowing a solution of 95% ethanol (200 ml), concentrated aqueous hydrochloric acid (8 ml), and the N-ethylnitrilium salt (prepared by 24 hr reflux of a solution of trimethylamine-cyanoborane (0.2 mol) and 400 ml of 1 N triethyloxonium tetraflouroborate in methylene chloride) to reflux for 48 hr. After neutralization with a saturated sodium bicarbonate solution and removal of ethanol at reduced pressure, the product was extracted from the aqueous solution with methylene chloride. Drying the organic portion over magnesium sulfate and solvent removal produced a yellow liquid. Purification by recrystallization from ethanol or ether or by sublimation afforded the ester as a white crystalline solid (9.9 g). Satisfactory carbon, hydrogen, nitrogen, and boron analysis were obtained. The $^1$H NMR signals (deuterochloroform) are those expected for the trimethylamine ($\delta$ 2.78, singlet) and ethyl ($\delta$ 1.2 triplet; $\delta$ 4.10, quartet) functionalities and strong B-H (2380 cm$^{-1}$) and C=O (1660 cm$^{-1}$) stretches were present in the IR spectrum.

3-Dimethylaminopropionitrile-cyanoborane

In a similar manner, NaBH$_3$CN (13.5 g, 215 mmol) and an equimolar amount of the amine hydrochloride (29.0 g) were allowed to react for 76 hr in refluxing THF. The mixture was filtered to remove NaCl and THF was removed from the filtrate at reduced pressure. The remaining viscous yellow oil was purified by dissolving it in H$_2$O (ca. 80 ml) followed by extraction of the aqueous solution with CHCl$_3$(3×60 ml). The combined CHCl$_3$ extracts were dried over MgSO$_4$ and filtered. Removal of CHCl$_3$ at reduced pressure afforded compound XIX as a clear oil which solidified on standing for several minutes. Yield 23.0 g, 78%.

Ethylenediamine-bis(cyanoborane)

As described above, NaBH$_3$CN (18.8 g, 300 mmol) and en.2HCl (19.9 g, 150 mmol) were allowed to react in refluxing THF for 100 hr. Removal of NaCl by filtration and evaporation of THF from the filtrate left a yellow colored solid. Recrystallization from ethanol/H$_2$O (2:1) and drying in vacuo (90° C. 24 hr) gave XX. Yield: 12.2 g, 59%.

TABLE I

Structures of Boron Analogs

| Compound No. | Compound | Synthetic Reference or Source |
|---|---|---|
| I | (CH$_3$)$_3$CNH$_2$ . BH$_3$ | Alfa Products |
| II | O(CH$_2$CH$_2$)$_2$NH . BH$_3$ | Alfa Products |
| III | (CH$_3$)$_3$N . BH$_3$ | Aldrich Chemicals |
| IV | (CH$_3$)$_2$NH . BH$_3$ | Aldrich Chemicals |
| V | (CH$_3$)$_3$N . BH$_2$CN | 1 |
| VI | (CH$_3$)$_2$NH . BH$_2$CN | 1 |
| VII | (CH$_3$)$_3$N . BH$_2$CON(H)CH$_2$CH$_3$ | 2 |
| VIII | (CH$_3$)$_3$N . BH$_2$COOH | 2 |
| IX | (CH$_3$)$_3$N . BH$_2$I | 3 |
| X | [Na{H$_3$N . BH$_2$(CN)}$_6$]I | |
| XI | [CH$_2$N(CH$_3$)$_2$ . BH$_2$CN]$_2$ | |
| XII | [CH$_2$N(CH$_3$)$_2$ . BH$_2$COOH]$_2$ | |
| XIII | [CH$_2$N(CH$_3$)$_2$ . BH$_2$CON(H)CH$_2$CH$_3$]$_2$ | |
| XIV | O(CH$_2$CH$_2$)$_2$N(CH$_3$) . BH$_2$CN | 1 |
| XV | C$_5$H$_5$N . BH$_2$CN | 1 |
| XVI | C$_5$H$_5$N . BH$_2$COOH | |
| XVII | H$_3$N . BH$_2$CN | 4 |
| XVIII | (CH$_3$)$_3$N . BH$_2$COOCH$_2$CH$_3$ | |
| XIX | NCCH$_2$CH$_2$N(CH$_3$)$_2$ . BH$_2$CN | |
| XX | (CH$_2$NH$_2$ . BH$_2$CN)$_2$. | |

1 Wisian-Neilson et al, Inorg. Chem., 17, 2327 (1978)
2 Spielvogel et al, J. Amer. Chem. Soc., 98, 5702 (1976)
3 Bratt et al, J. Chem. Soc. Dalton Trans., 2161 (1974)
4 McPhail et al, J. Chem. Research (S) 205 (M), 2601 (1978)

TABLE II

In Vivo Anti-Inflammatory Activity of Boron Analogs

| Compound No. | LD$_{50}$ mg/kg | Anti-inflammatory Screen 10 mg/kg × 2 | % Control Writhing Reflex 20 mg/kg | % Control Anti-Arthritic Screen 2.5 mg/kg/day |
|---|---|---|---|---|
| I | 16 | 41 | — | — |
| II | 475 | 55 | 15 | 33 |
| III | 740 | 65 | 47 | 12 |
| IV | 200 | 66 | 37 | 61 |
| V | 70 | 42 | 18 | 4 |
| VI | 39 | 49 | 24 | 25 |
| VII | 320 | 63 | 29 | 64 |
| VIII | 1800 | 79 | 29 | 53 |
| IX | 250 | 66 | 37 | 22 |
| X | 100 | 57 | 12 | 0 |
| XI | 200 | 95 | 76 | 77 |
| XII | >1000 | 58 | 54 | 19 |
| XIII | >1000 | 65 | 55 | 24 |
| XIV | 23 | 91* | 78* | 16 |
| XV | 25 | 83* | 80 | 45 |
| XVI | >200 | 74* | 53 | 44 |
| XVII | 30 | 51 | 50 | 32 |
| XVIII | >500 | 87 | 106 | 26 |
| XIX | 140 | 74 | 89 | 13 |
| XX | >150 | 87 | 95 | 100 |
| Indomethacin** | 28 | 22 | 43 | 27 |
| 6 MP | — | — | — | — |
| Control | — | 100 | 100 | 100 |

*⅓ dose
**tested at 10 mg/kg

TABLE III

Effects of Boron Analogs on in vitro Lysosomal Enzymatic Activities and cAMP Levels at 5 μ moles % Control

| | Liver | | PMNs | | |
|---|---|---|---|---|---|
| Compound No. | % Free Acid Phosphatase Activity, pH5 | % Free Cathepsin Activity, pH5 | % Free Acid Phosphatase Activity, pH5 | % Free Cathespin Activity, pH5 | cAMP Level |
| I | 77 ± 4 | 58 ± 5 | 100 ± 9 | 100 ± 4 | 58 |
| II | 75 ± 8 | 107 ± 6 | 79 ± 5 | 93 ± 7 | 107 |
| III | 72 ± 6 | 17 ± 4 | 57 ± 4 | 18 ± 3 | 145 |
| IV | 82 ± 3 | 67 ± 3 | 82 ± 6 | 65 ± 5 | 80 |
| V | 69 ± 4 | 0 ± 2 | 35 ± 5 | 4 ± 2 | 245 |
| VI | 73 ± 4 | 32 ± 5 | 89 ± 4 | 22 ± 1 | 98 |
| VII | 78 ± 7 | — | 100 ± 2 | 22 ± 5 | 98 |
| VIII | 82 ± 5 | 56 ± 6 | 50 ± 3 | 14 ± 4 | 99 |
| IX | 71 ± 6 | 14 ± 3 | 71 ± 5 | 40 ± 4 | 133 |
| X | 65 ± 3 | 3 ± 1 | 34 ± 6 | 0 ± 3 | 361 |
| XI | 80 ± 6 | 50 ± 7 | 84 ± 5 | 16 ± 5 | 94 |

TABLE III-continued

Effects of Boron Analogs on in vitro Lysosomal Enzymatic Activities and cAMP Levels at 5 μ moles % Control

| | Liver | | PMNs | | |
|---|---|---|---|---|---|
| Compound No. | % Free Acid Phosphatase Activity, pH5 | % Free Cathepsin Activity, pH5 | % Free Acid Phosphatase Activity, pH5 | % Free Cathespin Activity, pH5 | cAMP Level |
| XII | 69 ± 5 | 23 ± 6 | 84 ± 4 | 52 ± 4 | 155 |
| XIII | 74 ± 4 | — | 100 ± 7 | 70 ± 6 | 92 |
| XIV | 68 ± 7 | 13 ± 5 | 50 ± 3 | 37 ± 5 | 165 |
| XV | 79 ± 3 | 57 ± 4 | 57 ± 4 | 49 ± 7 | 110 |
| XVI | 77 ± 8 | 58 ± 4 | 100 ± 5 | 31 ± 4 | 100 |
| XVII | 75 ± 5 | 48 ± 6 | 100 ± 2 | 26 ± 4 | 93 |
| XVIII | — | — | — | 16 ± 3 | — |
| XIX | 66 ± 4 | 15 ± 3 | 100 ± 9 | 17 ± 5 | 199 |
| XX | 77 ± 8 | 80 ± 7 | 100 ± 10 | 57 ± 2 | 28 |
| Indomethacin | 86 ± 4 | 67 ± 6 | 100 ± 2 | 100 ± 1 | 80 |
| Control | 100 ± 7[a] | 100 ± 6[b] | 100 ± 8[c] | 100 ± 6[d] | 100[e] |

Footnotes to Table III
[a] 0.753 mg Pi released 1 hr/gm wet tissue
[b] 7.17 mg protein released 1 hr/gm wet tissue
[c] 0.26 μg Pi released 1 hr/$10^7$ cells
[d] 0.225 mg protein released 1 hr/$10^7$ cells
[e] 748 p mole cAMP/$10^7$ cells

TABLE IV

The Effects of Boron Analogs on in vitro Prostaglandin Synthesis and Oxidative Phosphorylation Processes % Control

| | | Oxidative Phosphorylation 5 μ moles | | | |
|---|---|---|---|---|---|
| | Prostaglandin | Succinate | | α Ketoglutarate | |
| Compound No. | Synthesis $10^{-6}$ M | State 4 | State 3 | State 4 | State 3 |
| I | 100 ± 3 | 118 ± 11 | 63 ± 8 | 160 ± 35 | 63 ± 14 |
| II | 100 ± 5 | 115 ± 15 | 66 ± 10 | 97 ± 29 | 50 ± 11 |
| III | 61 ± 3 | 117 ± 11 | 56 ± 12 | 71 ± 8 | 28 ± 10 |
| IV | 100 ± 5 | 119 ± 9 | 82 ± 4 | 67 ± 18 | 53 ± 16 |
| V | 59 ± 6 | 133 ± 20 | 51 ± 20 | 85 ± 21 | 42 ± 9 |
| VI | 63 ± 4 | 126 ± 19 | 61 ± 5 | 128 ± 25 | 45 ± 12 |
| VII | 100 ± 7 | 114 ± 13 | 74 ± 9 | 113 ± 37 | 45 ± 18 |
| VIII | 93 ± 3 | 122 ± 14 | 63 ± 4 | 127 ± 22 | 70 ± 20 |
| IX | 67 ± 5 | 120 ± 12 | 63 ± 9 | 102 ± 16 | 70 ± 13 |
| X | 42 ± 5 | 110 ± 5 | 31 ± 10 | 101 ± 25 | 37 ± 10 |
| XI | 85 ± 4 | 116 ± 8 | 122 ± 13 | 168 ± 38 | 106 ± 21 |
| XII | 60 ± 6 | 80 ± 11 | 57 ± 16 | 122 ± 15 | 48 ± 30 |
| XIII | 100 ± 4 | 117 ± 8 | 66 ± 8 | 162 ± 43 | 50 ± 24 |
| XIV | 38 ± 3 | 62 ± 10 | 36 ± 5 | 140 ± 47 | 51 ± 16 |
| XV | 58 ± 3 | 124 ± 16 | 57 ± 16 | 112 ± 42 | 52 ± 15 |
| XVI | 76 ± 5 | 110 ± 13 | 75 ± 15 | 109 ± 30 | 63 ± 15 |
| XVII | 55 ± 6 | 112 ± 7 | 60 ± 11 | 149 ± 27 | 40 ± 9 |
| XVIII | — | 119 ± 18 | 61 ± 19 | 126 ± 51 | 54 ± 8 |
| XIX | 53 ± 7 | 43 ± 16 | 24 ± 7 | 105 ± 33 | 33 ± 8 |
| XX | 81 ± 5 | 13 ± 5 | 10 ± 5 | 50 ± 18 | 25 ± 8 |
| Indomethacin ($10^{-4}$ M) | 64 ± 2 | — | — | — | — |
| Control | 100[a] | 100 ± 6[b] | 100 ± 4[c] | 100 ± 8[d] | 100 ± 9[e] |

Footnotes to Table IV
[a] 6564 dpm of PgE formed/hr/mg enzyme
[b] 9.19 μl $O_2$ consumed/hr/mg wet tissue
[c] 13.66 μl $O_2$ consumed/hr/mg wet tissue
[d] 3.38 μl $O_2$ consumed/hr/mg wet tissue
[e] 4.93 μl $O_2$ consumed/hr/mg wet tissue

We claim:

1. An amine borane compound selected from the group consisting of $[CH_2N(CH_3)_2.BH_2COOH]_2$, $[CH_2N(CH_3)_2.BH_2CON(H)CH_2CH_3]_2$,

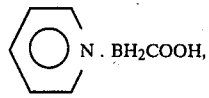

$(CH_3)_3N.BH_2COOCH_2CH_3$,
$NCCH_2CH_2N(CH_3)_2.BH_2CN$, and
$(CH_2NH_2.BH_2CN)_2$.

2. The compound of claim 1 which is $[CH_2N(CH_3)_2.BH_2COOH]_2$.

3. The compound of claim 1 which is $[CH_2N(CH_3)_2.BH_2CON(H)CH_2CH_3]_2$.

4. The compound of claim 1 which is

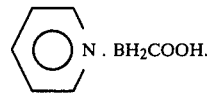

5. The compound of claim 1 which is $(CH_3)_3N.BH_2COOCH_2CH_3$.

6. The compound of claim 1 which is $NCCH_2CH_2N(CH_3)_2.BH_2CN$.

7. The compound of claim 1 which is $(CH_2NH_2.BH_2CN)_2$.

* * * * *